United States Patent
Anderson et al.

(10) Patent No.: US 9,147,110 B2
(45) Date of Patent: Sep. 29, 2015

(54) FIELD AND CROP EVALUATION TOOL AND METHODS OF USE

(71) Applicant: PIONEER HI BRED INTERNATIONAL INC, Johnston, IA (US)

(72) Inventors: Barry L. Anderson, Lake Crystal, MN (US); Chad C. Berghoefer, North Mankato, MN (US); Brent A. Brueland, Boone, IA (US); Neal A. Fitch, Grimes, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 14/246,804

(22) Filed: Apr. 7, 2014

(65) Prior Publication Data

US 2014/0301607 A1 Oct. 9, 2014

Related U.S. Application Data

(60) Provisional application No. 61/809,045, filed on Apr. 5, 2013.

(51) Int. Cl.
*G06K 9/00* (2006.01)
*G01N 33/00* (2006.01)

(52) U.S. Cl.
CPC ........ *G06K 9/00657* (2013.01); *G01N 33/0098* (2013.01)

(58) Field of Classification Search
CPC ............ G06K 9/0063; G06K 9/00657; G06K 2209/17; G06T 2207/30188; G06T 2207/30181
See application file for complete search history.

(56) References Cited

U.S. PATENT DOCUMENTS

| | | | |
|---|---|---|---|
| 7,343,341 B2 | 3/2008 | Sandor et al. | |
| 7,877,970 B1 | 2/2011 | Crosby | |
| 7,927,884 B2 | 4/2011 | Sullivan et al. | |
| 8,712,148 B2 * | 4/2014 | Paris et al. | 382/165 |
| 2002/0173979 A1 | 11/2002 | Daggett et al. | |
| 2004/0158478 A1 | 8/2004 | Zimmerman | |
| 2005/0098713 A1 | 5/2005 | Holland | |
| 2009/0009962 A1 | 1/2009 | Vinson et al. | |
| 2009/0099962 A1 | 4/2009 | Green et al. | |
| 2011/0299777 A1 * | 12/2011 | Tilton | 382/173 |
| 2012/0023884 A1 | 2/2012 | Spikes et al. | |
| 2013/0301870 A1 * | 11/2013 | Mow et al. | 382/100 |
| 2014/0212055 A1 * | 7/2014 | Boriah et al. | 382/224 |

FOREIGN PATENT DOCUMENTS

WO 2008/124474 A2 10/2008

OTHER PUBLICATIONS

Dickey et al ("Determining crop residue cover with electronic image analysis", 1989 ).*

(Continued)

*Primary Examiner* — Avinash Yentrapati

(57) ABSTRACT

A method for determining a percent ground cover over an area of land is provided. An image of the area of land is captured, and an area of interest within the image is defined. The area of interest image is converted to a gray scale image, a user-adjustable threshold is specified for distinguishing ground cover from soil and the percent ground cover present in the gray scale image is calculated and reported.

11 Claims, 3 Drawing Sheets

(56) References Cited

OTHER PUBLICATIONS

Liska, "Improvements in Life Cycle Energy Efficiency and Greenhouse Gas Emissions of Corn-Ethanol", Journal of Industrial Ecology, Retrieved from www.blackwellpublishing.com/jje, 17 pages. (2008).

Bjornsen, "Automatic Determination of Bacterioplankton Biomass by Image Analysis", Applied and Environmental Microbiology, Retrieved from http://aem.asm.org/ on Mar. 10, 2014, vol. 51 (6): 1199-1204 (1986).

Blaschke, "Object based image analysis for remote sensing", ISPRS Journal of Photogrammetry and Remote Sensing, vol. 65: 2-16 (2010).

Daughtry, et al, "Potential for Discriminating Crop Residues from Soil by Reflectance and Flourescence", Reprinted from Agronomy Journal, vol. 87 (2): 165-171 (1995).

Meyer, et al, "Electronic Image Analysis of Crop Residue Cover on Soil", Biological Systems Engineering: Papers and Publications, Retrieved from DigitalCommons@University of Nebraska—Lincoln, vol. 31(3): 968-973 (1988).

Moran, et al, "Opportunities and Limitations for Image Based Remote Sensing in Precision Crop Management", Remote Sens. Environ. vol. 61: 319-346 (1997).

Parton, et al, "Observations and Modeling of Biomass and Soil Organic Matter Dynamics for the Grassland Biome Worldwide", Global Chemical Cycles, vol. 7(4): 785-809 (1993).

Tackenberg, "A New Method for Non-destructive Measurement of Biomass, Growth Rates, Vertical Biomass Distribution and Dry Matter Content Based on Digital Image Analysis", Annals of Botany, Retrieved from www.aob.oxfordjournals.org, vol. 99: 777-783 (2007).

Roberts, et al, "Simultaneous Adoption of Herbicide-Resistant and Conservation-Tillage Cotton Technologies," Journal of Agricultural and Applied Economics, vol. 38 (3): 629-643.(Dec. 2006).

* cited by examiner

FIELD AND CROP EVALUATION TOOL AND METHODS OF USE

CROSS-REFERENCE TO RELATED APPLICATIONS

The present application claims priority from U.S. Provisional Application No. 61/809,045 filed Apr. 5, 2013, which is hereby incorporated herein by reference in its entirety.

FIELD OF THE INVENTION

The present invention relates to a method of evaluating a field or crops, and particularly a method for calculating a percent ground cover.

BACKGROUND

A number of land or crop management decisions rely on knowing an accurate percent ground cover present in a field. Traditionally, the percent ground cover in a field has been calculated manually by the "transect method," which involves identifying a boundary defining an area in the field, placing a tape measure, string, or similar object on the ground within the boundary, counting the amount of residue that lies below the placed object, and using the count to estimate the percent ground cover for the defined area. The transect method typically involves a rope with evenly spaced knots, and a user counts the number of times ground cover occurs directly below a knot to estimate the percent ground cover. As this method can be time consuming or inaccurate, an improved method for calculating the percent ground cover in a field is desired.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION

System

Figure 2:
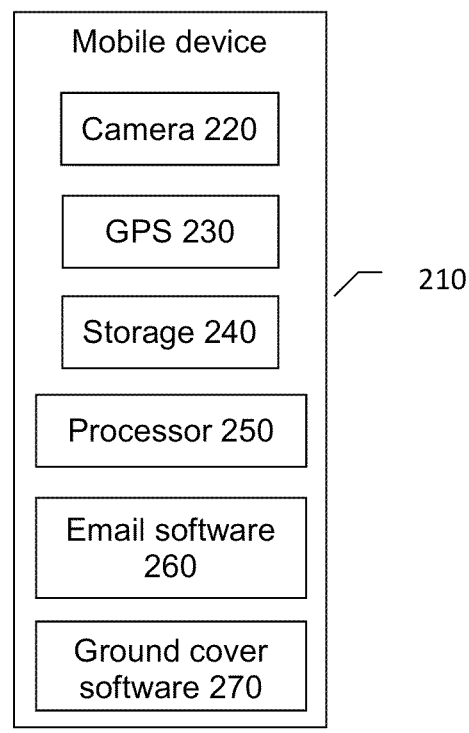
FIG. 2. is an illustration of an image capture device in accordance with an embodiment of the present invention.

Referring to FIG. 2, a mobile device 210 for determining a percent ground cover over an area of land 310 is illustrated. In one embodiment, mobile device 210 comprises an iPad, iPhone, iPod, other iOS device, tablet, mobile phone, or similar device.

Mobile device 210 comprises a processor component 250 configured to perform operations of mobile device 210.

Mobile device 210 may further comprise a built-in camera component 220 configured to capture images. Images captured be stored in internal storage components 240 of mobile device 210, and may be used by software applications operating on mobile device 210.

Mobile device 210 may further comprise a global positioning system (GPS) 230 configured to provide position information to components and software applications of mobile device 210.

A number of software applications may operate on mobile device 210. For example, email software 260 may be present on mobile device 210. A specialized percent ground cover calculation software application 270 may also operate on mobile device 210.

Method

Figure 1:
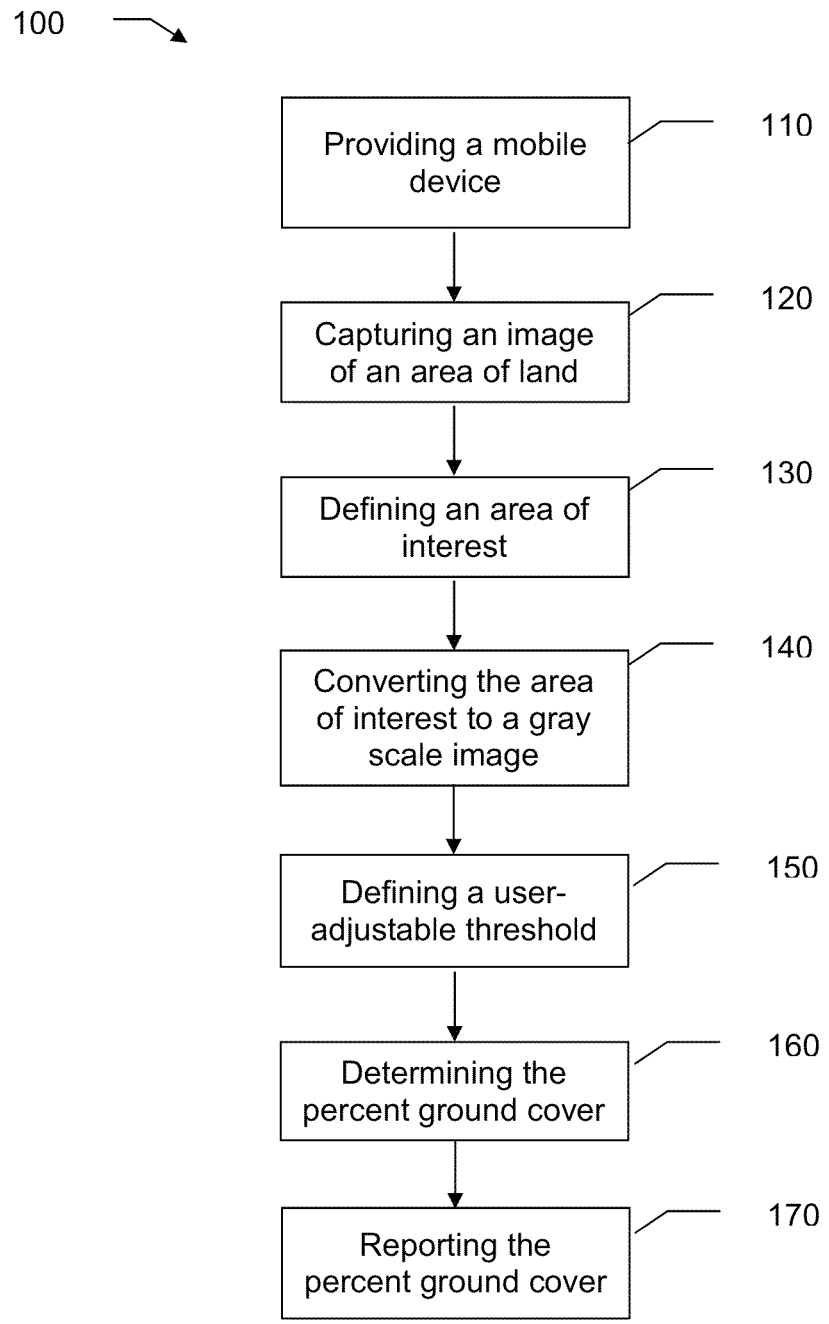
FIG. 1 is an illustration of method for determining a percent ground cover over an area of land in accordance with an embodiment of the present invention.
Figure 3:
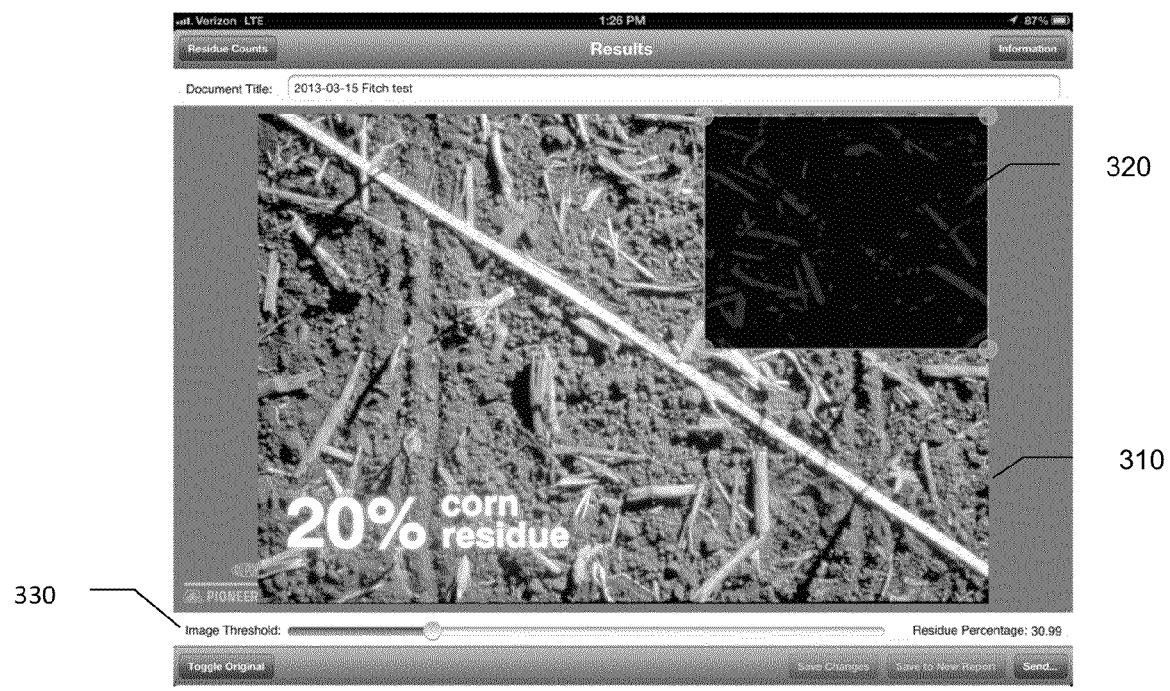
FIG. 3 is an illustration of an area of land for which a percent ground cover may be calculated in accordance with an embodiment of the present invention.

Referring to FIGS. 1 and 3, a method 100 for determining a percent ground cover over an area of land 310 is illustrated. A mobile device 210 is provided in step 110. In one embodiment, mobile device 210 comprises an iPad, iPhone, iPod, other iOS device, tablet, mobile phone, or similar device. Mobile device 210 comprises a built-in camera 220 configured to capture images.

In step 120, an image of an area of land 310, such as a crop field, is captured using the camera 220 of the mobile device 210. The captured image may be saved to the device's internal storage 240. Alternatively, the image may be processed without saving to the device's internal storage 240. Image processing techniques are applied to the captured image by the device's processor 250. The precise location where the image is captured may also be recorded using the global positioning system (GPS) 230 of mobile device 210.

In other embodiments, images may be captured using a separate image capture device that may comprise a digital camera, a video camera, or other camera. In some embodiments the image is saved to a storage device. In some examples the image comprises a screen grab or a frame grab. In other examples the image is first digitized or scanned to generate a digital image for storage and/or for analysis. The image may comprise a series of images, a video, or an image captured from a video. In such other embodiments, image processing may be accomplished using a separate computing device.

In step 130, the user may define or select an area of interest 320 comprising a portion of the image 310 for which percent ground cover is to be calculated. In one embodiment, the user may draw a boundary box or a freeform boundary using the touchscreen or other input means of mobile device 210. The entire image may be selected, or the user may select a portion of the image for performing the percent ground cover calculation.

In step 140, image processing techniques are applied to the area of interest 320. In one embodiment, the image 310 or the area of interest 320 is converted to a gray scale image. To convert to a gray scale image, the green strength of each pixel is extracted and used. As corn residue tends to begin as yellow material, the green channel (of red-green-blue) should provide the best information specific to corn residue. Other areas of the image will tend to be more white (bluer) or brown (redder). The image becomes gray scale based on green values of 0 to 255. Some ground highlighting and rocks are automatically reduced by this operation. The image pixels are thresholded by changing all pixels below a user-specified cutoff value to be set to black. This removes most of the ground, leaving only the ground cover as the ground cover is usually the brighter parts of the image. A cross shaped structuring element of 5 pixels in size is selected to be used as a growth shape for the now-white pixels. The concept here is that the user will tend to select pixels by sliding the threshold until the selected areas are within the visible residue. This naturally leads to some of the corn residue information getting removed from the image. The use of a cross shape is intended to automatically bring back some of this lost information when it is placed at each white pixel. In some examples, the residue is from another crop plant, including but not limited to alfalfa, barley, canola, cotton, millet, oats, rice, safflower, sorghum, soybean, sugar cane, sunflower, tobacco, wheat, and the like. In some examples the residue may include residue from non-crop plants, such as weeds, or volunteer plants from a previous growing season. In other examples, the residue or ground cover can be a mixture of materials such as mulch, compost, or manure.

The percent ground cover is calculated in step 160. Image processing techniques may be implemented by the processor 250 of the device 210 to determine the percentage of white or black pixels present in the image 310 or area of interest 320 to reach a calculation of the percent ground cover present in the image 310 or area of interest 320. As soil colors and conditions may vary widely across geographic locations, the contrast of the image 310 or area of interest 320 may be adjusted in step 150 to allow for the image processing techniques applied to differentiate between ground cover and soil. The user interface for enhancing contrast may take the form of a manual image threshold slider bar 330 or other input means that a user adjusts until a desired contrast is reached. Alternatively, contrast enhancement may occur automatically. Contrast enhancement may be accomplished automatically through histogram equalization, or other image processing technique. Alternatively, a user may enter the soil type present at the field location, and the contrast calibration may be performed automatically based on the field type. The image pixels are examined within the selected rectangle and counted. A percent ground cover is calculated based on the number of pixels above the threshold. The calculated percentage is now used to look up a calibrated value in a previously generated spline curve that was manually generated through experimental data. The resulting value is the final residue percentage presented to the user. The calibration curve was manually constructed by comparing the raw pixel count percentages with actual experimental results from a set of real world images. These results were graphed in a stand-alone graphic tool (any curve graphing tool can be used.) Some small manual adjustments were made, and some image data points were rejected, to wind up with a relatively smooth and consistent curve. A set of points were then selected from the curve. These points are used to construct a standard cubic spline curve inside the percent ground cover application. Computed percentages are then looked up in the spline curve to determine the final result.

Once the percent ground cover is calculated, the calculated percent ground cover is reported in step 170. Captured images and calculated percent ground cover may be saved to the device's internal storage 240, sent in an email in text format, .PDF format, or other suitable format, or opened in an application for immediate viewing as shown in FIG. 3. A formatted report may be generated. The images, calculated percent ground cover, report, or any combination of the three may be emailed to a user using an email software application 260 operating on the device 210 to provide information about the area of land. The recipient of the email may then make a number of decisions or take a number of actions using the provided information. The images, calculated percent ground cover, report, or any combination of the three may also be uploaded to a server for use in other applications.

Alternatively, the percent ground cover may be calculated using an existing image stored on the device or an image captured on a separate image capture device. The method may also be implemented using a laptop computer, desktop computer, server, or other arrangement.

The described method is capable of making rapid measurements of ground cover. The rapid measurement technique enables a larger number of calculations to be made. In addition, by calculating the percent ground cover in this manner, greater accuracy is achieved over manual calculation, for example, by including small pieces of ground cover that a human using visual inspection may omit Once at least one percent ground cover calculation has been performed, a user may perform additional calculations, or may view stored results.

In one embodiment, ground cover comprises stover, residue, or other plant material remaining on the ground following a grain harvest. In other embodiments, ground cover may comprise other plant material (leaves, stalks, roots, etc.), compost, manure, or other material.

Applications

The calculation may be performed at any time and for any crop. Often the percent ground cover is calculated in fall following a grain or stover harvest or in spring before tillage. The calculated percent ground cover may be used to guide a number of decisions. Decisions may be based directly on the percent ground cover, or may be based on probable conditions such as probable soil moisture, probable soil temperature, stover residue, probable pest, weed, or disease pressure, etc. estimated from the percent ground cover.

In one embodiment, a user may calculate percent ground cover following a stover harvest. Stover refers to non-grain plant material that remains on the ground following a grain harvest. Stover may be harvested for use in cellulosic ethanol production, or for other applications. If the calculated percent ground cover following stover harvest is below a certain threshold, the user may reduce the amount of stover harvested in future growing seasons. Likewise, if the calculated percent ground cover is above a certain threshold, the user may increase the amount of stover harvested in future growing seasons. By adjusting stover management plans, an optimal amount of stover may be left on the ground to ensure that an optimal amount of stover remains on the ground. For example, a user wants to leave enough stover to provide nutrients to the soil and prevent soil erosion; however, too much stover can increase disease or insect pressure or delay planting dates due to decreased soil temperature or increased soil moisture. The information gained helps users understand and ultimately make decisions regarding the sustainability and value associated with stover harvest.

In another embodiment, the device may transmit or store the calculated percent ground cover for purposes of the user's participation in conservation programs.

In another embodiment, a user may calculate the percent ground cover to determine an optimal tillage method. For example, a user may modify a tillage plan by using rippers or coulters to rip up the ground cover material if the percent ground cover is high. If a large number of stalks remain in the field, the user may employ stalk chopping equipment to further break down the stalks. Conversely, a user may be able to reduce tillage if the percent ground cover is low, which can have environmental benefits such as reducing soil erosion and reducing fuel usage. If tillage can be avoided completely due to low percent ground cover, the user also benefits from reduced soil compaction.

In another embodiment, a user may calculate how much of a material, for example mulch, compost, or manure, has been distributed on the ground.

In another embodiment, a user may calculate percent ground cover as a step in an input application process. As the amount of ground cover increases, disease, fungus, or other pressures may increase. For example, excess ground cover may harbor insects or diseases, or overwintered insect eggs may be present on the excess ground cover. A user may calculate the percent ground cover as described previously, determine whether insect or disease pressure or other risk is present, and apply a fungicide, pesticide, or other input if the percent ground cover exceeds a threshold. The amount of ground cover may also be indicative of soil nutrient needs. For example, residue plays an important role in replenishing soil nutrients; therefore, if the percent ground cover is low, then a user may apply additional fertilizer or other nutrients to the soil to compensate for the lack of ground cover.

In another embodiment, the method may be enhanced to use additional image processing techniques to determine the number of pieces of ground cover or the average size of the pieces. The type of material that comprises the ground cover, for example stalk or leaf material, may also be determined using image processing techniques. Different sizes of ground cover will break down differently. Likewise, different types of ground cover break down differently. A user may use different tillage equipment if the ground cover is of sufficient size or of a type that does not break down adequately on its own.

A user may calculate percent ground cover at any time. For example, a user may calculate percent ground cover when there are no plants in the field to determine how much residue is on the ground. In another embodiment, a user may calculate percent ground cover when plants are present at any time during plant development to measure over row or between row ground cover. If the method is applied when no plants are not present in the field, the percent ground cover typically indicates the amount of residue or other material on the ground. If the method is applied when plants are present in the field, the percent ground cover may indicate the amount of residue on the ground, or may indicate stand count.

When plants are present in the field, the method may also be used to determine when the canopy closes. For example, when the ground cover exceeds a given threshold, then this indicates that the canopy has closed, and ground equipment should no longer be driven through the field. This is particularly useful in situations where the image is captured autonomously, for example by unmanned aerial system (UAS), unmanned aerial vehicle (UAV), or by satellite image, and the determination of whether the canopy is closed can be made without a trip to the field.

In another embodiment, a user may calculate the percent ground cover as described above, and then may choose and plant a particular crop or crop variety based on the calculated percent ground cover. The quantity of ground cover can impact the rate at which the soil warms. Using a soil temperature model and/or weather data, a user may predict soil temperatures at various planting dates, and choose a cold tolerant crop or variety, or a crop or variety that is suited to the predicted growing season length. Likewise, a user may choose a planting date based on the percent ground cover, for example, by delaying planting if the percent ground cover is high, indicating that the soil temperature may not have reached the desired temperature.

The quantity of ground cover can also impact the moisture level of the soil. In another embodiment, a user may calculate the percent ground cover as described above, and then choose and plant a particular crop or crop variety suited to the moisture level of the soil. For example, a user may choose a moisture tolerant crop or variety if the percent ground cover indicates high soil moisture, or may choose a drought tolerant variety if the percent ground cover indicates a low moisture level. A user may also choose seed treatments suited to moist conditions if the percent ground cover is high, or may apply an input such as a fungicide to improve germination rate if the percent ground cover is high. A user may also choose and plant a pest or disease tolerant crop or variety if the percent ground cover is high and indicative of increased pest or disease pressure.

In another embodiment, a user may increase or otherwise vary the planting density based on the percent ground cover.

In another embodiment, a user may calculate percent ground cover as described above, and may change planting equipment based on the calculation. For example, a user may use rippers or coulters if the percent ground cover is high.

In another embodiment, the method may be used to determine the amount of lodging, or downed stalks. This determination may be made after a storm or other event likely to cause lodging. Alternatively, the determination may be made in a research scenario by subjecting a known crop variety to high winds and assessing the lodging resistance of the variety. For example, an image capture device may be mounted on a device for applying a wind force to plants such as the device described in U.S. Pat. No. 7,412,880. When mounted to such a wind force device, an image may be captured following application of the wind force, and image processing techniques applied to automatically calculate the lodging or other damage that has been caused by the wind force. Alternatively, images may be continuously captured while the wind force is being applied, and the wind force device may be turned off automatically if a threshold of damage is achieved.

In any of the above mentioned applications of the method, the user may use additional information to inform decisions made based on the percent ground cover. For example, the user may incorporate information such as soil type, soil characteristics, previous crop, previous management practices, management zones, multiple map boundaries, field topography, field elevation, crop type, product list, irrigation status, EnClass classification, climate, weather, crop model, insurance information, regulatory constraints, previous inputs, etc. to enhance decisions made using percent ground cover.

What is claimed is:

1. A method for determining a percent ground cover over an area of land comprising:
   providing a mobile device;
   capturing an image of the area of land using a camera installed on the mobile device;
   defining an area of interest within the image using a ground cover software application operating on the mobile device;
   converting the area of interest to a gray scale image using the ground cover software application, wherein the converting to gray scale comprises converting the green channel to white pixels;
   enhancing white pixels in the area of interest with a structuring element used as a growth shape;
   defining a threshold for distinguishing ground cover from soil using the ground cover software application;
   determining the percent ground cover present in the gray scale image using the ground cover software application; and
   reporting the percent ground cover.

2. The method of claim 1 wherein determining the percent ground cover present in the gray scale image comprises calculating a number of pixels with values exceeding the defined user-adjustable threshold, and dividing the number of pixels with values exceeding the defined user-adjustable, threshold by a total number of pixels in the area of interest.

3. The method of claim 1 wherein the area of interest comprises a subset of pixels present in the image of the area of land.

4. The method of claim 1 wherein the area of interest comprises the image of the area of land.

5. The method of claim 1 wherein reporting the percent ground cover comprises displaying a value representing the percent ground cover within the ground cover software application.

6. The method of claim 1 wherein reporting the percent ground cover comprises creating a document indicating the percent ground cover present in the area of interest.

7. The method of claim 6 further comprising attaching the document to an email and sending the entail using an email software application on the mobile device.

8. The method of claim 1 wherein reporting the percent ground cover comprises transmitting the area of interest to another software application for further processing.

9. The method of claim 1, wherein the growth shape is a cross shaped structuring element of 5 pixels in size.

10. The method of claim 1, wherein the threshold is determined automatically.

11. The method of claim 1, wherein the threshold is adjustable by a user.

* * * * *